(12) United States Patent
Nerin et al.

(10) Patent No.: US 7,724,371 B2
(45) Date of Patent: May 25, 2010

(54) DEVICE FOR EXAMINING A FLUID BY UNIFORM ILLUMINATION USING A CONFIGURED LIGHT GUIDE

(75) Inventors: Philippe Nerin, Nages et Solorgues (FR); Paul Moreno, Montpellier (FR); Didier Cremien, Sussargues (FR)

(73) Assignee: Horiba ABX SAS, Montpellier (FR)

( * ) Notice: Subject to any disclaimer, the term of this patent is extended or adjusted under 35 U.S.C. 154(b) by 393 days.

(21) Appl. No.: 11/719,620

(22) PCT Filed: Nov. 7, 2005

(86) PCT No.: PCT/FR2005/002769

§ 371 (c)(1),
(2), (4) Date: May 17, 2007

(87) PCT Pub. No.: WO2006/053960

PCT Pub. Date: May 26, 2006

(65) Prior Publication Data

US 2009/0161107 A1      Jun. 25, 2009

(30) Foreign Application Priority Data

Nov. 18, 2004  (FR) .................................. 04 12246

(51) Int. Cl.
*G01N 21/59* (2006.01)
(52) U.S. Cl. ...................................... 356/436; 356/441
(58) Field of Classification Search ......... 356/432–444, 356/246, 244, 128, 336; 385/33, 146
See application file for complete search history.

(56) References Cited

U.S. PATENT DOCUMENTS

| | | | | |
|---|---|---|---|---|
| 4,497,577 A | * | 2/1985 | Sato et al. | 356/336 |
| 4,671,657 A | * | 6/1987 | Calvani et al. | 356/484 |
| 4,711,126 A | * | 12/1987 | Houpt et al. | 73/293 |
| 4,752,131 A | | 6/1988 | Eisenlauer et al. | |
| 4,907,878 A | * | 3/1990 | Arditty et al. | 356/128 |
| 5,046,853 A | * | 9/1991 | Hemel et al. | 356/440 |
| 5,071,217 A | * | 12/1991 | Birch | 385/33 |
| 5,636,017 A | * | 6/1997 | Bruno et al. | 356/246 |
| 5,983,120 A | * | 11/1999 | Groner et al. | 600/310 |
| 6,445,492 B1 | * | 9/2002 | Nielsen et al. | 359/334 |
| 7,379,651 B2 | * | 5/2008 | Abu-Ageel | 385/146 |
| 2006/0232779 A1 | * | 10/2006 | Shaw | 356/436 |

FOREIGN PATENT DOCUMENTS

| | | |
|---|---|---|
| EP | 0 801 295 | 10/1997 |
| EP | 1 298 460 | 4/2003 |
| WO | 85 05680 | 12/1985 |

* cited by examiner

*Primary Examiner*—Sang Nguyen
(74) *Attorney, Agent, or Firm*—Oblon, Spivak, McClelland, Maier & Neustadt, L.L.P.

(57) ABSTRACT

An optical device for examining a fluid including a measuring space including a compulsory passage for the fluid to be examined, at least one source delivering a selected light to an optical illuminator serving to collect at least part of the light having traversed the compulsory passage and to deliver the selected light to analyze the collected light so as to deliver signals representing data borne by the collected light. The optical illuminator includes a first light guide including one end, opposite the source, and configured to deliver the light, derived from the source, in accordance with a selected geometry to illuminate the compulsory passage in a substantially uniform manner and under a substantially constant intensity.

14 Claims, 2 Drawing Sheets

DEVICE FOR EXAMINING A FLUID BY UNIFORM ILLUMINATION USING A CONFIGURED LIGHT GUIDE

FIELD OF INVENTION

The invention relates to the field of fluid analysis and more particularly the devices used for analysing (or examining) fluids using a light.

DISCUSSION OF THE BACKGROUND

In certain fields, such as medical analysis (blood counts or flow cytometry), for example, fluid examining devices are used which are based on the interaction between the different components of a fluid and a light.

These devices generally comprise a measuring space having a compulsory passage for the fluid to be examined, a source supplying a selected light to optical illuminating means charged with illuminating the compulsory passage with this light, optical means serving to collect at least some of the light that has passed through the compulsory passage and deliver it to means serving to analyse the collected light in order to deliver the signals representative of data which it carries. A device of this kind is described in particular in French patent FR 2653885.

The data carried by the collected light relates for example to the forms and/or coefficients of reflection and/or coefficients of diffraction and/or coefficients of absorption of the various components of the fluid being examined. The data are obtained for example by transmission measurements well known in the art which need not be described here.

In the case of haematological analysis, for example, the examining device has to be able to distinguish blood cells automatically according to their category (chiefly leukocytes (or white corpuscles) and erythrocytes (or red corpuscles)), and the variety within their category (for example, lymphocytes, monocytes, neutrophils and eosinophils among the leukocytes, or reticulocytes among the erythrocytes).

In order that the examining device can distinguish between the different components suspended in the fluid to be examined, the components have to receive substantially the same intensity of light over the same period of time when passing through the compulsory passage in the measuring space.

In order to obtain a substantially uniform distribution of light over the entire surface defined by the compulsory passage it has been proposed to use an incoherent source such as an incandescent source coupled with a diaphragm and a so called Köhler optical assembly. This assembly consists in using a first lens to form the image of the source in the plane of the pupil of a second lens tasked with forming the image of a diaphragm in the plane of the compulsory passage of the measuring space.

A first drawback of this Köhler assembly device resides in the fact that it has a poor photometric yield, i.e. very little light is concentrated on the measuring zone, thus making certain analyses difficult, especially the analysis of biological cells.

In order to increase the yield it is possible to use high power sources, typically of several dozen watts. However, such sources generate considerable amounts of heat which are liable to interfere with the analyses and incur considerable costs.

A second drawback of this Köhler assembly device resides in the fact that it requires a set of lenses which cannot be easily be placed in the vicinity of the measuring space. In fact, as is known in the art, the smaller the size of the fluid expulsion nozzle, the larger it is possible to make the numerical aperture of the light be and the better the photometric balance. Consequently, for a fluid expulsion nozzle of a given diameter, the closer the illuminating optics are to the compulsory passage, the better the photometric balance.

SUMMARY OF THE INVENTION

As no examining device known hitherto is entirely satisfactory, the invention therefore sets out to improve the situation.

For this purpose it proposes a device for optically examining a fluid, comprising a measuring space including a compulsory passage for the fluid to be examined, at least one source delivering a selected light to optical illuminating means serving to illuminate the compulsory passage with this light, optical means serving to collect at least some of the light which has passed through the compulsory passage and to deliver it to means serving to analyse the collected light so as to deliver signals representing data carried by said light.

This device is characterised in that its optical illuminating means comprise first light guiding means having one end, opposite the source, configured to deliver the light, derived from the source, in accordance with a selected geometry so that it illuminates the compulsory passage in a substantially uniform manner and at a substantially constant intensity.

The device according to the invention may have additional features which can be taken separately or together, particularly:

- its first light guiding means may take the form of an optical fibre,
  - the configured end of the optical fibre comprises for example a core micro-machined to a selected shape over a selected length in order to allow total internal reflection of the light and to deliver a light beam the cross section of which has the selected geometry (for example substantially rectangular),
  - the optical fibre may be of the multimodal type, optionally with an index difference,
- the source may be of the polychromatic type,
- the source may be of the quasi monochromatic type,
- in the presence of a plurality of (quasi) monochromatic sources, multiplexing means may be provided, comprising an input coupled to the output from each of these (quasi) monochromatic sources and an output coupled to a supply end of the first light guiding means, opposite their configured end.
- correcting means may be installed upstream of the compulsory passage and tasked with correcting the chromatic aberrations which are introduced by the rest of the optical illuminating means,
- the optical collecting means may comprise second light guiding means having a collecting end oriented towards the compulsory passage,
  - the second light guiding means are constructed for example in the form of an optical fibre,
  - each source may be located outside an axis passing through the configured end of the first light guiding means, the compulsory passage and the collecting end of the second light guiding means. In this case, each source and/or at least part of the analysing means may be implanted in an electronic card,
- each source may, for example, be a light-emitting diode, a laser diode, a laser, an incandescent lamp or a discharge lamp.

The invention is particularly well suited to the medical analysis of samples, particularly flow cytometry and blood counts, although this is not restrictive.

BRIEF DESCRIPTION OF THE DRAWINGS

Further features and advantages of the invention will become apparent from a study of the detailed description that follows, together with the attached drawings, wherein.

The attached drawings may not only serve to supplement the invention but may in certain cases also contribute to its definition.

DISCUSSION OF PREFERRED EMBODIMENTS

Figure 1:
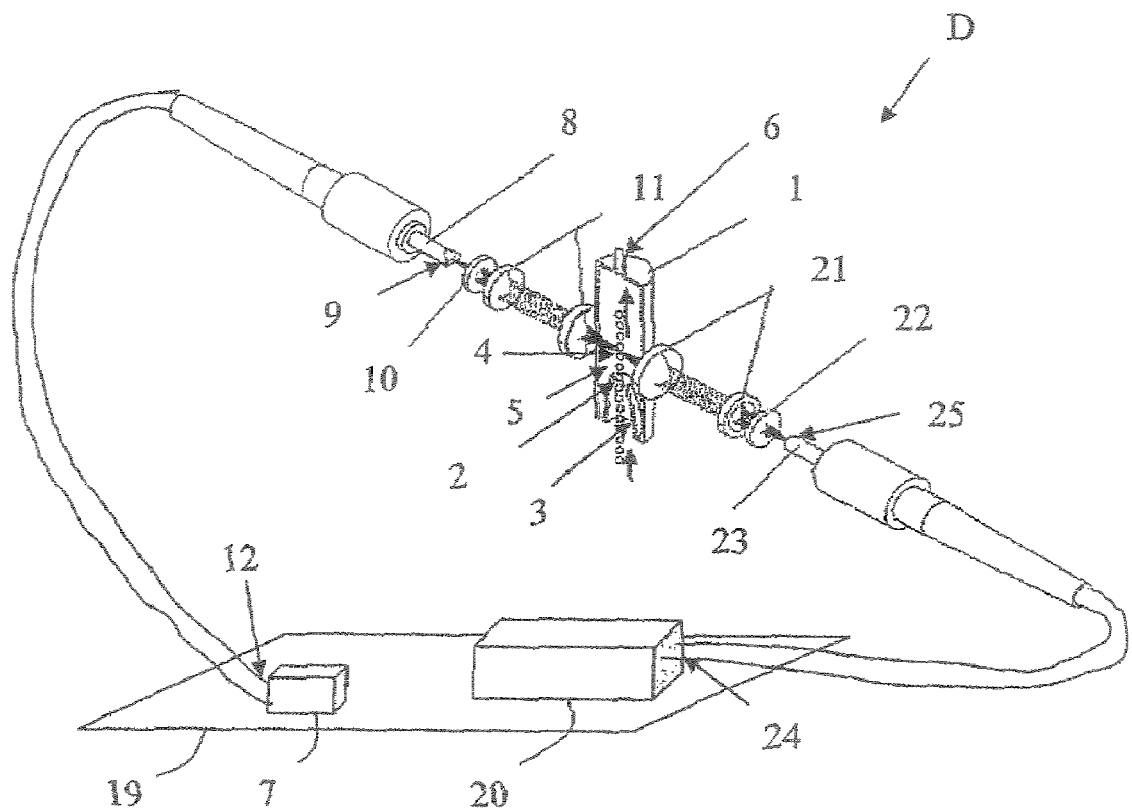
FIG. 1 schematically shows an embodiment of an optical fluid examining device according to the invention.

Reference will be made first of all to FIGS. 1 and 2 in order to describe an embodiment of an optical fluid examining device D according to the invention.

In the description that follows it is assumed that the device D is intended for examining (or analysing) a fluid in the form of a haematological sample in order to carry out a blood count. However, the invention is not limited either to this type of fluid or to counting. In fact it relates to all types of fluid, and all types of analysis, and especially flow cytometry.

As shown in FIG. 1, an examining device D according to the invention comprises first of all a measuring vessel 1, preferably of the type known as a "flow sleeve" vessel as described for example in French patent FR 2653885.

In simple terms, a vessel 1 of this kind comprises an inner wall in which is placed a focusing nozzle 2, generally made of sapphire and defining a calibrated orifice typically 60 μm in diameter. The wall defines an inner recess 3 in which is placed a very small capillary (not shown) typically 200 μm in diameter, the end of which is located opposite the nozzle 2 and at a short distance from it. This capillary is intended to channel the fluid to be examined upstream of the nozzle 2 in order to be carried in the form of a primary flux by a secondary buffering fluid circulating in said inner recess 3 around the capillary.

The vessel 1 also comprises, downstream of the nozzle 2, a measuring space 4 comprising a compulsory passage 5 (or measuring zone, or measuring window) for examination of the fluid which is delivered by the nozzle 2.

Because of the very small size of the nozzle 2 and the hydrodynamic buffering technique used, the blood cells (of the fluid to be examined) emerge one by one at the compulsory passage 5 and can thus be subjected at least to optical analysis, as will be seen hereinafter.

The fluid to be examined is collected in the upper part of the vessel 1 by a collecting duct 6, shown in part.

The optical analysis described above is carried out by means of an interaction between the cells (components) of the fluid under examination and a light beam at the compulsory passage 5 of the measuring space 4.

The light beam which illuminates the compulsory passage 5 is delivered by optical illuminating means (hereinafter referred to as illumination optics) supplied with light by at least one source 7.

The light delivered by the source 7 is chosen in particular in accordance with the cells which are to be analysed and/or the dye or dyes which may be used to stain certain varieties (or sub-varieties) of cells. It should be recalled that frequently fluorescent dyes are used for cell analysis. In fact, when the dye contained in the stained cells absorbs the (or one of the) emission wavelength(s) of the source 7, it almost instantly (typically in $10^{-8}$ s) and isotropically re-emits a radiation known as fluorescence with a longer wavelength than the light radiation absorbed. Some of this fluorescence can therefore be collected, either at 90° to the optical analysis axis or parallel to this axis (epifluorescence).

Depending on the requirements, either a source 7 delivering a quasi monochromatic light or a source 7 delivering a polychromatic light will therefore be selected.

The quasi monochromatic source 7 used may be, for example, a light emitting diode (or LED). However, it is also possible to use a laser diode or a laser the emission wavelength and emission power of which will if necessary permit fluorescing of stained components which are to be analysed.

The polychromatic source 7 used may be, for example, an incandescent lamp or arc lamp or numerous (quasi) monochromatic sources.

According to the invention, the illumination optics comprise at least first light guiding means 8 having a first end 9, opposite the source 7, configured to deliver the light derived from the source 7 in accordance with a selected geometry (or shape) such that it illuminates the compulsory passage 5 in a substantially uniform manner and at a substantially constant intensity.

In other words, the first end 9 is configured so as to deliver the light in the form of a light beam having a uniformity of intensity over a surface of a selected shape (or geometry), in cross-section.

It is important to note that the selected shape and surface of the cross-section of the light beam delivered by the first light guiding means 8 are not necessarily identical to those which the light beam has when it reaches the compulsory passage 5. In fact, as shown in FIG. 1, the illumination optics may comprise, in addition to the first light guiding means 8, optical elements serving to channel the beam at the compulsory passage 5 and optionally to bring it into the for at of the compulsory passage 5. Thus, a regulating plate 10, for example of the type having parallel surfaces, may be provided at the exit from the first light guiding means 8, this plate being intended to allow fine control of the lateral positioning of the light beam relative to the compulsory passage 5 and hence relative to the fluid which is to be examined. Projection optics 11 may also be provided, consisting for example of a pair of lenses, e.g. of the anamorphic type, placed between the regulating plate 10 and the vessel 1, and intended to focus the light beam at the compulsory passage 5.

Figure 2A:
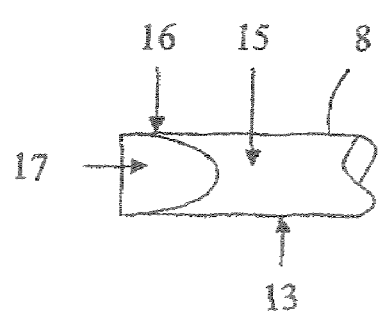
FIGS. 2A and 2B show an example of a configured end of an optical illuminating fibre of the type known as "cylindrical lensed", in plan view and front view, respectively, FIG. 3 schematically shows the shape of the cross section of the light beam obtained at the compulsory passage by means of the optical fibre in FIG. 2.
Figure 2B:
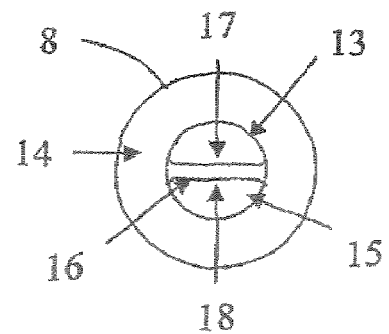

As is better shown in FIGS. 2A and 2B, the first light guiding means 8 are preferably in the form of an optical fibre, a second end 12 of which, opposite the first configured end 9, is coupled to the output of the source 7.

For example, the first configured end 9 of the optical fibre 8 comprises a portion 13 in which the sheath 14 has been omitted over a selected length and the outer surface of the core 15 has preferably been covered (with the exception of an end portion 16) with a reflective metallic material. The end portion 16 of the core 15 is for example micro-machined in a selected shape over a selected length in order to allow total internal reflection of the light and deliver the light beam in the selected form (or geometry) mentioned previously (in its cross-section). By micro-machining the end portion 16 of the core 15 it is possible in fact to preserve only its central part which, in the case of so called index-difference light guides, is the region in which the light has a homogeneous field.

In the embodiment shown in FIGS. 2A and 2B, the end portion 16 of the core 15 is micro-machined so as to deliver a light beam having a substantially rectangular cross-section. The micro-machining consists here in defining two bevelled faces 17 and 18 in the core 15, these faces being for example bevelled at angles of about 50 to 55°, which terminates slightly before their intersection in order to form a substantially rectangular end part. The bevelled faces 17 and 18 may also have an outer coating which will stop the refracted light.

This type of micro-machined first end 9 is manufactured for example by the Japanese company Namiki. More precisely, the embodiment shown corresponds to an end of an optical fibre 8 known as a "cylindrical lensed" type (or CLF standing for "Cylindrical Lensed Fibre") the technical details of which can be found in particular on the internet website "www.namiki.co.jp/nqt/tp14.html".

Figure 3:
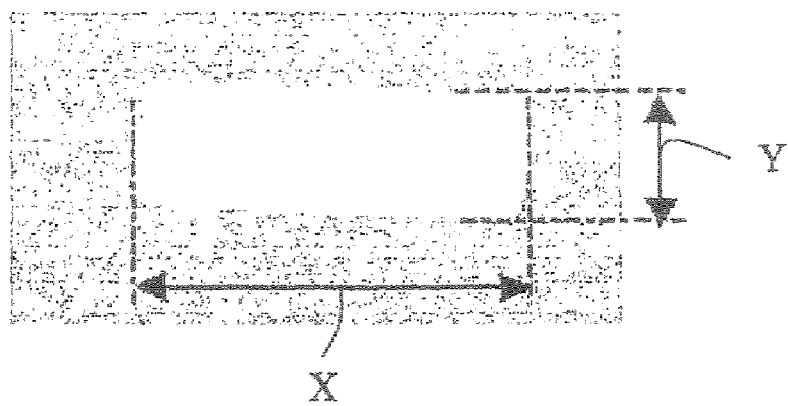

Thanks to this type of micro-machining, and using optical elements of the type presented hereinbefore (regulating plate 10 and projection optics 11), the cross-section of the light beam may be substantially rectangular in shape at the compulsory passage 5, as shown in FIG. 3. For example, starting with a micro-machined optical fibre 8 having a rectangular end portion 16 measuring approximately 155 µm×55 µm, it is possible to obtain a rectangular illumination surface with a length X equal to about 105 µm and a width Y equal to about 33 µm.

The optical fibre 8 may for example be of the multimodal type, optionally with an index difference. It is possible for example to use the optical fibres produced by 3M, Lucent Technology and OPS.

By using an optical fibre 8 it is possible to move the light source 7 on to an electronic card 19 on which at least some of the analysing means 20, to which reference will be made hereinafter, may also be implanted. The displacement of the source 7 out of the optical axis of the measuring vessel 1 (i.e. the axis passing through the configured end 9 of the first light guiding means 8, the compulsory passage 5 and the collecting end 25 of the second light guiding means 23 which will be described hereinafter) is particularly advantageous as it enables heat sources to be kept out of the immediate surroundings of the vessel 1.

Moreover, as a result of the invention, the examining device D is substantially simpler than an equivalent device comprising a Köhler assembly both in mechanical terms and in optical terms, given that the first end 9 of the optical fibre 8 may be substituted for the pair of aspherical lenses in the Köhler assembly and there is no longer any need to use a condenser and a diffuser.

Moreover, the use of an optical fibre 8 enables the measuring vessel 1 to be miniaturised.

Furthermore, owing to the very great precision of the micro-machining and its high level of reproducibility, it is possible to do away with some of the micrometric regulating means for the measuring vessel 1, thus increasing the reproducibility of performance provided by the examining devices D.

It is important to note that in the presence of a polychromatic source 7, correction optics (not shown) can be provided in addition to the illumination optics 8-12, with the intention of eliminating at least some of the chromatic aberrations introduced by the illumination optics. In addition, these same optics may be designed so as to correct the geometric aberrations introduced by the walls of the vessel and by the thickness of fluid passing through. This correction may be made using optics having one or more aspherical dioptres, at least one of which may have a diffraction grid intended to correct the chromatism.

Furthermore, the use of an optical fibre 8 enables the examining device D to be equipped with a number of (quasi) monochromatic light sources emitting at different wavelengths. In this case, each source is coupled to one of the inputs of a multiplexer, the output of which is coupled to the input of the optical fibre 8.

As mentioned previously, the interaction between the light beam delivered by the illumination optics, described hereinbefore, and the fluid to be examined takes place at the compulsory passage 5 in the measuring vessel 1. The results of this interaction are analysed by conventional analysing means 20, such as for example one or more photoelectric detectors, not described here, via optical collecting means 21-25 situated downstream of the measuring vessel 1.

More precisely in the non-restrictive embodiment shown in FIG. 1, the optical collecting means (or more simply the collection optics) comprise a pair of lenses 21, for example of the anamorphic type, intended to collect the light which has passed through the measuring space 4, followed by a regulating plate 22, for example of the type having parallel surfaces, intended for precise introduction of the light collected in the second light guiding means 23, the output 24 of which is coupled to the detection means intended for analysis 20.

The principle of (photo-)detection is well known. It should simply be mentioned that each component (or cell or particle) in the fluid to be examined, stained or otherwise, which reaches the compulsory passage 5, absorbs and/or diffracts and/or reflects light, shaped by the illumination optics (and chiefly by the first light guide means 8 thereof) and having a substantially constant uniformity and intensity over substantially the entire surface of said compulsory passage 5. These interactions help to reduce the continuous component of the photoelectric signal which is delivered by the photoelectric detectors (in the absence of any interaction), which is indicated by electrical impulses the respective shapes and durations of which are characteristic of the components which have interacted with the illuminating light.

Figure 4:
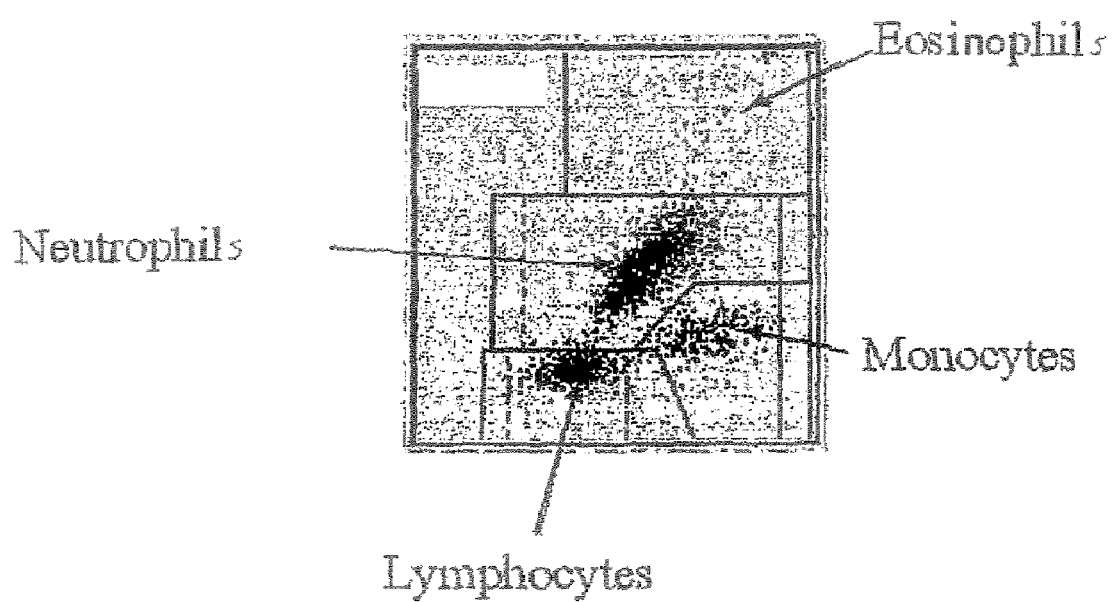
FIG. 4 is an image illustrating the results of a blood analysis obtained using an examining device according to the invention.

An example of an image representing a distribution matrix of the leukocyte populations in a blood sample, obtained with an examining device D according to the invention, is shown in FIG. 4. The top right hand part of the figure shows a population of eosinophils, while the central part shows a population of neutrophils, the bottom right hand corner shows a population of monocytes and the lower central part shows a population of lymphocytes.

Preferably, the second light guiding means 23 are produced in the form of an optical fibre, a first end 25 of which is supplied with collected light (in this case by the regulating plate 22) while a second end defines the exit 24.

By means of this collecting optical fibre 23 it is possible to displace the photodetector or photodetectors out of the optical axis of the measuring vessel 1, for example on to the electronic card 19, and hence further simplify the assembly both mechanically and optically.

The invention is not restricted to the embodiments of a optical fluid examining device described hereinbefore, solely by way of example, but encompasses all the variants which could be envisaged by the skilled man within the scope of the claims that follow.

The invention claimed is:

1. A device for optically examining a fluid, comprising:
a measuring space having a compulsory passage for a fluid that is to be examined;
at least one source configured to deliver a selected light;
optical illuminating means supplied with light by the source and to illuminate the compulsory passage with the light according to selected geometric characteristics;
optical collecting means to collect at least some of the light that has passed through the compulsory passage and to deliver collected light to a selected location; and
analyzing means supplied with the light collected by the optical collecting means and to analyze the collected light so as to deliver signals representing data which the collected light carries,
wherein the optical illuminating means comprises first light guiding means having one end opposite the source and configured to deliver the light derived from the source in accordance with a selected geometry so that the light illuminates the compulsory passage in a substantially uniform manner and at a substantially constant intensity, and
wherein the first light guiding means include an optical fiber, wherein the configured end of the optical fiber comprises a core micro-machined in a selected shape along a selected length so as to allow total internal reflection of the light and preserve a region in which the light has a homogeneous field to deliver a light beam with a cross-section having the selected geometry, and wherein the selected geometry is substantially rectangular in shape.

2. A device according to claim 1, wherein the optical fiber is of multimodal type.

3. A device according to claim 2, wherein the multimodal optical fiber has an index difference.

4. A device according to claim 1, wherein the source is of polychromatic type.

5. A device according to claim 1, wherein the source is of quasi monochromatic type.

6. A device according to claim 1, comprising at least two sources of a quasi monochromatic type emitting at different wavelengths.

7. A device according to claim 6, further comprising multiplexing means having an input coupled to the output of each of the quasi monochromatic sources and an output coupled to a supply end of the first light guiding means, opposite the configured end.

8. A device according to claim 4, further comprising correcting means installed upstream of the compulsory passage and configured to correct chromatic aberrations introduced by the optical illuminating means.

9. A device according to claim 1, wherein the optical collecting means comprises second light guiding means having a collecting end oriented towards the compulsory passage.

10. A device according to claim 9, wherein the second light guiding means include an optical fiber.

11. A device according to claim 9, wherein the source is located outside an axis passing through the configured end of the first light guiding means, the compulsory passage, and the collecting end of the second light guiding means.

12. A device according to claim 1, further comprising an electronic card on which are implanted each source and/or at least some of the analyzing means.

13. A device according to claim 1, wherein each source is selected from a group comprising at least light emitting diodes, laser diodes, lasers, incandescent lamps, and discharge lamps.

14. Use of an examining device according to claim 1 in the field of medical analysis of samples, or flow cytometry, or haematological counting.

* * * * *